United States Patent [19]

Sarantakis

[11] 4,178,284
[45] Dec. 11, 1979

[54] OCTAPEPTIDES

[75] Inventor: Dimitrios Sarantakis, West Chester, Pa.

[73] Assignee: American Home Products Corporation, New York, N.Y.

[21] Appl. No.: 968,658

[22] Filed: Dec. 11, 1978

[51] Int. Cl.$^2$ .................... C07C 103/52; A61K 37/00
[52] U.S. Cl. .............................. 260/112.5 R; 424/177
[58] Field of Search .................. 260/112.5 R; 424/177

[56] References Cited

U.S. PATENT DOCUMENTS 4,127,533  11/1978  Cog et al. ..................... 260/112.5 R

Primary Examiner—Delbert R. Phillips
Attorney, Agent, or Firm—Richard K. Jackson

[57] ABSTRACT

Octapeptide derivatives of Met- and Leu-enkephalin C-terminally modified by addition of L-Lys-Gly-L-Glu-OH or L-Lys-Gly-L-Gln-OH release endogenous growth hormone without analgesia or side effects elicited by the enkephalins or morphine.

10 Claims, No Drawings

OCTAPEPTIDES

SUMMARY OF THE INVENTION des-(6-28)-β-Endorphin and derivatives thereof are intracerebroventricular analgesic agents which release growth hormone where peripherally administered. The compounds are therefore useful in treatment of dwarfism in the juvenile and as agents for promoting healing of wounds, bones and in maintenance of tissue integrity of animals. The novel compounds and their precursor octapeptide intermediates form the subject of this invention.

SPECIFICATION

In accordance with this invention there is provided a group of novel octapeptides of the formula:

H-Tyr-X$_1$-Gly-Phe-X$_2$-Lys-Gly-X$_3$-OH in which
X$_1$ is Gly or D-Ala;
X$_2$ is Met, Leu, D-Met or D-Leu; and
X$_3$ is Glu or Gln;
or a pharmaceutically acceptable salt thereof.

These compounds are structurally reminiscent of the naturally occurring enkephalins H—Tyr—Gly—Gly—Phe—Met—OH
                                         Met-enkephalin
and    H—Tyr—Gly—Gly—Phe—Leu—OH
                                         Leu-enkephalin isolated and characterized by Hughes et al., Nature 258 577(1975), which are known to possess analgesic activity when administered intracerebroventricularly, Belluzzi et al., Nature 260 625(1976) and to stimulate the release of prolactin in vivo, Lien et al., Life Sciences 19 837 (1976).

Met-enkephalin is known to constitute the first five amino acids of the β-endorphin molecule:

H-Tyr-Gly-Gly-Phe-Met-Thr-Ser-Glu-Lys-Ser-Gln-
Thr-Pro-Leu-Val-Thr-Leu-Phe-Lys-Asn-Ala-Ile-
Ile-Lys-Asn-Ala-His-Lys-Lys-Gly-Gln-OH.

β-Endorphin itself has been isolated and characterized by Bradbury et al. Nature 206 793 (1976) and Li et al. Proc. Natl. Acad. Sci. U.S.A. 73 1145 (1976). β-Endorphin has been shown to possess potent analgesic activity by intravenous injection, Tseng et al., Nature 263 239 (1976) and intracerebral administration, Loh et al., Proc. Natl. Acad. Sci. U.S.A. 73 2895 (1976). βEndorphin has also demonstrated growth hormone and prolactin release stimulation in the rat, Dupont et al. Proc. Natl. Acad. Sci. U.S.A. 74 358 (1977) and Rivier et al., Endocrinology 100 238 (1977).

The compounds of this invention incorporate the C-terminal tripeptide of β-endorphin as a C-terminal modification of both Met- and Leu-enkephalin and derivatives of those known analgesics. Surprisingly, the peripheral analgesic property of β-endorphin was lost in the compounds of this invention.

The non-toxic acid addition salts are pharmaceutically acceptable and are prepared from the polypeptide by conventional methods. Illustrative acids from which such salts are prepared include both organic and inorganic acids such as hydrochloric, hydrobromic, sulfuric, sulfonic, polyphosphoric, phosphoric, nitric, tartaric, fumaric, glycolic, citric, maleic, succinic, acetic, propionic, benzoic, ascorbic, and the like.

In addition, this invention provides novel intermediates of the formula:

R-Tyr(R$^1$)-X$_1$-Gly-Phe-X$_2$-Lys(R$^2$)-Gly-Glu(α-R$^3$)-Z in which
X$_1$ and X$_2$ are defined above and
R is an α-amino protecting group;
R$^1$ is a hydroxy protecting group;
R$^2$ is an amino protecting group;
R$^3$ is a carboxy protecting group; and
Z is a benzhydrylamine modified, hydroxymethyl or chloromethyl modified polystyrene resin support.

Each of the protecting groups and the polystyrene resin supports are known, the latter being commercially available from various sources.

Illustrative of the applicable α-amino protecting groups represented by R are the groups:
formyl, trifluoroacetyl, phthalyl, toluenesulfonyl, o-nitrophenylsulfenyl, benzyloxycarbonyl, p-methoxybenzyloxycarbonyl, p-nitrobenzyloxycarbonyl, 2-bromobenzyloxycarbonyl, 2-chlorobenzyloxycarbonyl, 1-(p-biphenylyl)-1-methyl-ethoxy carbonyl, tert-butyloxycarbonyl, diisopropylmethoxycarbonyl, allyloxycarbonyl, 2,2,2-trichloroethoxycarbonyl, amyloxycarbonyl, α,α-dimethylbenzyloxycarbonyl, α,α-dimethyl-3,5-dimethoxybenzyloxycarbonyl, benzhydryloxycarbonyl, 9-fluoroenylmethoxycarbonyl, isobornyloxycarbonyl and adamantyloxycarbonyl.

Applicable amino protecting groups for lysine are:
formyl, trifluoroacetyl, phthalyl, toluenesulfonyl, o-nitrophenylsulfenyl, benzyloxycarbonyl, p-methoxybenzyloxycarbonyl, p-nitrobenzyloxycarbonyl, 2-bromobenzyloxycarbonyl, 2-chlorobenzyloxycarbonyl, 1-(p-biphenylyl)-1-methyl-ethoxy carbonyl, tert-butyloxycarbonyl, diisopropylmethoxycarbonyl, allyloxycarbonyl, 2,2,2-trichloroethoxycarbonyl, amyloxycarbonyl, α,α-dimethylbenzyloxycarbonyl, α,α-dimethyl-3,5-dimethoxybenzyloxycarbonyl, benzhydryloxycarbonyl, 9-fluorenylmethoxycarbonyl, isobornyloxycarbonyl, adamantyloxycarbonyl; The selection of such a side chain amino protecting group is not critical except that it must be one which is not removed during cleavage of the α-amino protecting group during the synthesis until the peptide of the desired amino acid sequence is obtained. Hence, the α-amino protecting and side chain amino protecting group cannot be the same;

The protecting group for the hydroxyl group of the tyrosine moiety may be benzyloxycarbonyl, tert-butyl or benzyl. The preferred protecting group is benzyl. The selection of this protecting group is not critical except that it must not be removed during cleavage of the α-amino protecting group during the synthesis until the peptide of the desired amino acid sequence is obtained;

The protecting group for the α-carboxy group of glutamic acid is any ester or anhydride which is not removed during removal of the α-amino protecting groups. Preferably the benzyl ester is employed to protect the carboxy group.

The compounds of this invention are prepared by conventional solid phase or liquid phase (classical) techniques well known to the peptide chemist. Illustrative of the solid phase synthesis technique is the following example of the preparation of des-(6-28)-β-endorphin.

EXAMPLE 1 tert-Butyloxycarbonyl-O-2,6-dichlorobenzyl-L-tyrosyl-glycyl-glycyl-L-phenylalanyl-L-methionyl-ε-2-chlorobenzyloxycarbonyl-L-lysyl-glycyl-α-benzyl-γ-L-glutamyl-benzyhydrylamine polystyrene resin support The title peptidoresin is prepared by treating a benzhydrylamine resin (Beckman, 5 g.) in accordance with Schedule A for the incorporation of Boc-Glu(OH)OBzl, Boc-Gly-OH, Boc-Lys-(ClZ)-OH, Boc-Met-OH, Boc-Phe-OH, Boc-Gly-OH and Boc-Tyr(Cl$_2$Bzl)-Gly-OH. The initial coupling of Boc-Glu(OH)OBzl with the benzhydrylamine resin is via the γ-carboxy group to afford the intermediate

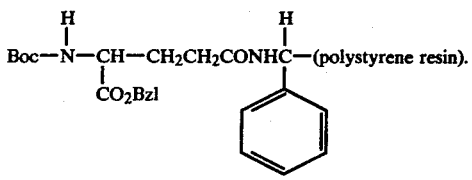

Schedule A
1. Wash with CH$_2$Cl$_2$×3.
2. Treat with TFA-CH$_2$Cl$_2$-EDT (1:1:5%, v/v) for 5 min.
3. Treat as in 2 for 25 min.
4. Wash with CH$_2$Cl$_2$×3.
5. Wash with DMF.
6. Treat with 12% TEA in DMF twice for 3 min.
7. Wash with DMF.
8. Wash with CH$_2$Cl$_2$×3.
9. Treat with 4 equivalents of the corresponding amino acid derivative in CH$_2$Cl$_2$—DMF and stir for 5 min.
10. Add in two portions 5 equivalents of DIC dissolved in CH$_2$Cl$_2$ and over a period of 30 min. Reaction time 6 hours.
11. Wash with DMF×3.
12. Wash with CH$_2$Cl$_2$ × 3.
13. Test ninhydrin reaction according to Kaiser et al., Annal. Biochem. 34, 595 (1970). In case of incomplete reaction repeat lines 9 to 13 as above.

L-Tyrosyl-glycyl-glycyl-L-phenylalanyl-L-methionyl-L-lysyl-glycyl-L-glutamine diacetate The peptidoresin (8 g) was then mixed with anisole (15 ml) and treated with liquid HF for 45 minutes in an ice-bath. The excess HF was removed as fast as possible (ca. 60 minutes) under vacuo and the residue was taken in 10% aq. AcOH then filtered. The filtrate was treated with Bio Rad AG 3(acetate form) and then lyophilized to yield 1.3 g of crude material. This crude material was applied onto a column of Sephadex G-15 (2.5×90 cm) and eluted with 10% aq. AcOH. The material which emerged in fractions (5.5 ml each) 39-59 was pooled and lyophilized to yield 660 mg of impure material. This material was applied onto a column of Sephadex 625 (2.5×60 cm) which was equilibrated first with the lower phase of the biphasic system, n-butanol-water-gl. acetic acid, 4:5:1, v/v, then with the upper phase of the above system the title octapeptide emerged in fractions 63-73. Yield 185 mg.

TLC, Avicel precoated glass plates, R$_f$(BWA, 4:1:1) 0.25; Amino acid analysis: Glu (1) 1.06, Gly (3) 3, Met (1) 0.90, Tyr(1) 0.96, Phe (1) 1.03, Lys (1) 1.04, NH$_3$ (1) 1.30.

The procedure for preparing the corresponding compounds where X$_3$ is glutamic acid is substantially identical to that illustrated above, with the exception that the polystyrene resin support is either chloromethylated or hydroxymethylated polystyrene conventionally employed in the solid phase synthesis of polypeptides.

The sequential build-up of the polypeptides is the same when employing either the benzhydrylamine modified resin or the hydroxymethyl or chloromethyl modified resin. Introduction of Boc-Leu-OH, Boc-D-Met-OH or Boc-D-Leu-OH into the solid phase reactor as the fourth amino acid reactant affords the corresponding compounds where X$_2$ represents Leu, D-Met or D-Leu. Similarly, introduction of Boc-D-Ala-OH as the seventh amino acid reactant affords those compounds where X$_1$ is D-Ala.

EXAMPLE 2 tert-Butyloxycarbonyl-0,2,6-dichlorobenzyl-L-tyrosyl-D-alanyl-glycyl-L-phenylalanyl-D-methionyl-ε-2-chlorobenzyloxycarbonyl-L-lysyl-glycyl-α-benzyl-γ-L-glutamic acid hydroxymethyl polystyrene resin ester Chloromethylated polystyrene resin (Lab Systems, Inc.) was esterified with Boc-Glu(OH)OBzl to afford the intermediate

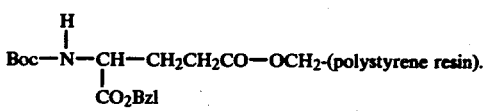

Subsequent coupling of Boc-Gly-OH, Boc-Lys(ClZ)-OH, Boc-D-Met-OH, Boc-Phe-OH, Boc-Gly-OH, Boc-D-Ala-OH and Boc-Tyr(Cl$_2$Bzl)-OH in accordance with Schedule A followed by cleavage from the resin and deprotection with purification as detailed in Example 1 yields the octapeptide:

EXAMPLE 3

H-Tyr-D-Ala-Gly-Phe-Met-Lys-Gly-Gln-OH

Following the procedure of Example 1, a benzhydrylamine resin is treated in accordance with Schedule A for the incorporation of Boc-Glu(OH)OBzl, Boc-Gly-OH, Boc-Lys(ClZ)-OH, Boc-Met-OH, Boc-Phe-OH, Boc-Gly-OH, Boc-D-Ala-OH and Boc-Tyr(Cl$_2$Bzl)-OH. The intermediate tert-butyloxycarbonyl-O-2,6-dichlorobenzyl-L-tyrosyl-D-alanyl-glycyl-glycyl-L-phenylalanyl-D-methionyl-ε-2-chlorobenzyloxycarbonyl-L-lysyl-glycyl-α-benzyl-γ-L-glutamylbenzhydrylamine polystyrene resin is deprotected and the product collected and purified in accordance with the second paragraph of Example 1 to yield the title octapeptide.

EXAMPLE 4

H-Tyr-D-Ala-Gly-Phe-Met-Lys-Gly-Glu-OH

Following the procedure of Example 2, a chloromethylated resin is treated with Boc-Glu(OH)OBzl, Boc-Gly-OH, Boc-Lys(ClZ)-OH, Boc-Met-OH, Boc-Phe-OH, Boc-Gly-OH, Boc-D-Ala-OH and Boc-Tyr(Cl$_2$Bzl)-OH, seriatim, in accordance with Schedule A. The fully protected intermediate peptidoresin is deprotected and the product purified to yield the title compound.

EXAMPLE 5

H-Tyr-Gly-Gly-Phe-Leu-Lys-Gly-Gln-OH

Following the procedure of Example 1, a benzhydrylamine resin is treated in accordance with Schedule A for the incorporation of Boc-Glu(OH)OBzl, Boc-Gly-OH, Boc-Lys(ClZ)-OH, Boc-Leu-OH, Boc-Phe-OH, Boc-Gly-OH, Boc-Gly-OH and Boc-Tyr(Cl$_2$Bzl)-OH. The fully protected intermediate peptidoresin is deprotected and the product purified to yield the title compound.

EXAMPLE 6

H-Tyr-D-Ala-Gly-Phe-Leu-Lys-Gly-Glu-OH

Following the procedure of Example 2, a chloromethylated resin is treated with Boc-Glu(OH)OBzl, Boc-Gly-OH, Boc-Lys(ClZ)-OH, Boc-Leu-OH, Boc-Phe-OH, Boc-Gly-OH, Boc-D-Ala-OH and Boc-Tyr(Cl$_2$Bzl)-OH, seriatim, in accordance with Schedule A. The title compound is obtained by deprotecting the peptidoresin followed by recovery and purification of the octapeptide by the method illustrated in the second paragraph of Example 1.

EXAMPLE 7

H-Tyr-D-Ala-Gly-Phe-D-Leu-Lys-Gly-Gln-OH

To a solid phase reactor containing a benzhydrylamine resin there is serially introduced, following the procedure of Schedule A, Boc-Glu(OH)OBzl, Boc-Gly-OH, Boc-Lys(ClZ)-OH, Boc-D-Leu-OH, Boc-Phe-OH, Boc-Gly-OH, Boc-D-Ala-OH and Boc-Tyr(CL$_2$Bzl)-OH. The intermediate peptidoresin is conventionally deprotected and purified to yield the title compound.

As growth hormone releasing agents, the compounds of this invention exhibit the advantage of peripheral activity without evidencing analgesia or the side effects attending the use of large amounts of the enkephalin, their super-agonists or morphine. Illustrative of the growth hormone releasing ability of the compounds of this invention is the activity of des-(66-88)-$\beta$-endorphin, representative of the other compounds, which at 2 milligrams per kilogram caused growth hormone release to result in a serum concentration of 380±124 ng/ml. as related to the control concentration of 55±8 ng/ml. at a confidence level of p<0.05, following the procedure of Lien et al. Febs. Letters 88 208–210 (1978). Thus, the compounds of this invention induce the release of growth hormone at a level comparable to that of morphine without the analgesic effects and side-effects of morphine.

Thus, the compounds of this invention are useful in any therapeutic treatment in which an increase of endogenous growth hormone (somatotropin) is desired. For example, it is known that the time taken to mend broken bones can be dramatically shortened with administration of growth hormone from exogenous sources. An increase of endogenously produced growth hormone would be similarly disposed to increase such healing rates. Likewise, in other application requiring treatment for maintenance of the integrity of bodily tissues such as in certain diseases of aging (senility), wound healing, etc. an increase in growth hormone is an indicated beneficial treatment. Obviously, in the treatment of dwarfism of the juvenile, which is based upon a deficiency of endogenous growth hormone, where that problem results from insufficient releasing hormone, the compounds of this invention may be employed in the same manner as somatotropin.

The compounds of this invention may be administered to warm-blooded mammals orally, sublingually, subcutaneously, intramuscularly, intravenously, etc. They may be administered in any suitable form for the specific route desired. Thus, tablets containing conventional adjuvants are applicable for oral administration. Intravenous, subcutaneous and intramuscular administration is readily achieved with carriers such as isotonic saline, phosphate buffered solutions and the like. The specific dosage and administration regimen must be individualized by the physician for the patient based upon the problem being treated, the route of administration, degree of response desired, severity and term of the disease or injury, and similar considerations.

What is claimed is:

1. A compound of the formula

H-Tyr-X$_1$-Gly-Phe-X$_2$-Lys-Gly-X$_3$-OH in which
  X$_1$ is Gly or D-Ala
  X$_2$ is Met, Leu, D-Met or D-Leu, and
  X$_3$ is Glu or Gln
or a pharmaceutically acceptable salt thereof.

2. The compound of claim 1 which is

H-Tyr-Gly-Gly-Phe-Met-Lys-Gly-Gln-OH or a pharmaceutically acceptable salt thereof.

3. The compound of claim 1 which is

H-Tyr-D-Ala-Gly-Phe-Met-Lys-Gly-Gln-OH or a pharmaceutically acceptable salt thereof.

4. The compound of claim 1 which is

H-Tyr-D-Ala-Gly-Phe-Met-Lys-Gly-Glu-OH or a pharmaceutically acceptable salt thereof.

5. The compound of claim 1 which is

H-Tyr-Gly-Gly-Phe-Leu-Lys-Gly-Gln-OH or a pharmaceutically acceptable salt thereof.

6. The compound of claim 1 which is

H-Tyr-D-Ala-Gly-Phe-Leu-Lys-Gly-Glu-OH or a pharmaceutically acceptable salt thereof.

7. The compound of claim 1 which is

H-Tyr-D-Ala-Gly-Phe-D-Met-Lys-Gly-Glu-OH or a pharmaceutically acceptable salt thereof.

8. The compound of claim 1 which is

H-Tyr-D-Ala-Gly-Phe-D-Leu-Lys-Gly-Gln-OH or a pharmaceutically acceptable salt thereof.

9. A compound of the formula

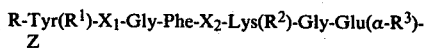
R-Tyr(R$^1$)-X$_1$-Gly-Phe-X$_2$-Lys(R$^2$)-Gly-Glu($\alpha$-R$^3$)-Z in which R is an α-amino protecting group;
R¹ is a hydroxy protecting group;
R² is an amino protecting group;
R³ is a carboxy protecting group;
X₁ is Gly or D-Ala;
X₂ is Met, Leu, D-Met or D-Leu; and
Z is a benzhydrylamine modified, a hydroxymethyl or a chloromethyl modified polystyrene resin support.

10. A compound of claim 9 in which R is tert-butyloxycarbonyl, R¹ is 2,6-dichlorobenzyl, R² is 2-chlorobenzyloxycarbonyl, R³ is benzyl and Z is a benzhydrylamine polystyrene resin.

* * * * *